United States Patent [19]

Stump

[11] 4,279,260
[45] Jul. 21, 1981

[54] OCCLUSAL INSTRUMENT

[76] Inventor: Lee K. Stump, 2314 K St., Belleville, Kans. 66935

[21] Appl. No.: 79,791

[22] Filed: Sep. 28, 1979

[51] Int. Cl.³ .............................................. A61B 5/10
[52] U.S. Cl. ...:.............................. 128/774; 33/174 D
[58] Field of Search ............. 128/774, 777; 33/174 D

[56] References Cited

U.S. PATENT DOCUMENTS

| | | | |
|---|---|---|---|
| 1,976,045 | 10/1934 | Sorenson | 33/174 D |
| 2,048,989 | 7/1936 | Baribeau | 33/174 D |
| 2,053,810 | 9/1936 | Bisel | 33/174 D |
| 3,394,459 | 7/1968 | Grant | 33/174 D |

*Primary Examiner*—William E. Kamm
*Attorney, Agent, or Firm*—Robert E. Breidenthal

[57] ABSTRACT

An occlusal instrument having indicia whereby all adjustments can be readily replicated, such adjustments being the relatively vertical position of three measuring means, with one of such means being adjustably extensible rearwardly; both of the other means being adjustably spreadable laterally, and one of such means being adjustable as to its angle of contact with the head about a lateral axis.

8 Claims, 6 Drawing Figures

OCCLUSAL INSTRUMENT

The present invention relates to new and useful improvements in occlusal instruments such as enable accurate replication of any predetermined lower jaw position as may be necessary in the making of dentures, performing bone or joint surgery or in the making of a facial restoration for cosmetic or any other purpose.

Rather than belabor those knowledgeable in the art with an exposition of the need and purposes of occlusal instruments and as to prior proposals as to possible structures of such instruments, an appreciation of such background matters can be readily obtained by the uninitiated by referring to prior U.S. patents, such as U.S. Pat. No. 2,107,534, entitled Face Meter, which issued to Houser on Feb. 8, 1939; U.S. Pat. No. 1,679,748, entitled Dental Appliance for Indicating the Outline of the Face, which issued to Stratton on Aug. 7, 1928; U.S. Pat. No. 1,662,670, entitled Measuring Instrument, which issued to Harter on Mar. 13, 1928. Also of interest is U.S. Pat. No. 2,552,385, entitled Face Meter, which issued to Scott on May 8, 1951; U.S. Pat. No. 1,944,601, entitled Dental Dimensionator, which issued to Gulick on Jan. 23, 1934; U.S. Pat. No. 1,976,045, entitled Occlusal Instrument, which issued to Sorenson on Oct. 9, 1934; U.S. Pat. No. 1,901,724, entitled Measuring Appliance, which issued to Bennett on Mar. 14, 1933; and U.S. Pat. No. 3,224,096, entitled Dental Articulator, which issued to Stuart on Dec. 21, 1965.

Broadly, the invention is in an occlusal instrument, an upstanding elongated standard adapted to be positioned in spaced relation at the front of and in the medial plane of a patient's head, said standard carrying orienting means adapted to engage spaced regions of the patient's face, said orienting means comprising uppermost, intermediate and lowermost measuring means mounted on the standard for movement relative to each other in the direction of the longitudinal extent of the standard, a first indicia means for enabling reading of the relative positions of the uppermost, intermediate and lowermost measuring means along the extent of the standard whereby such relative positions can be replicated, each of said measuring means extending rearwardly from the standard and terminating in patient contacting means, at least one of said measuring means being provided with means for varying the rearward extent and the spacing of its contacting means from the standard, a second indicia means for enabling replication of the extent of said one measuring means, and at least one of the other measuring means including a pair of horizontally spaced and rearwardly extending arms with the face contacting means of such measuring means including symmetrical parts disposed at the rearmost extremities of the arms, means carried by and movable with said one of the other measuring means for enabling horizontal and lateral movement of the arms relative to the standard, whereby the horizontal and lateral spacing of the said symmetrical parts can be varied, a third indicia means for enabling replication of the horizontal and lateral positions of the arms relative to the standard.

Various other important aspects of the invention involve the manner of mounting the various movable measuring means and the face contacting portions thereof, both for lateral and medial plane movements. Also deemed an important aspect of the invention is the provision of a pivotally mounted face contacting portion provided with indicia whereby the angle at which such portion contacts the face is measured for convenient subsequent replication.

These and other important aspects and features of the invention will readily be appreciated on reference to the following description of a preferred embodiment thereof, such description being given in connection with the accompanying drawings, wherein.

Figure 1:
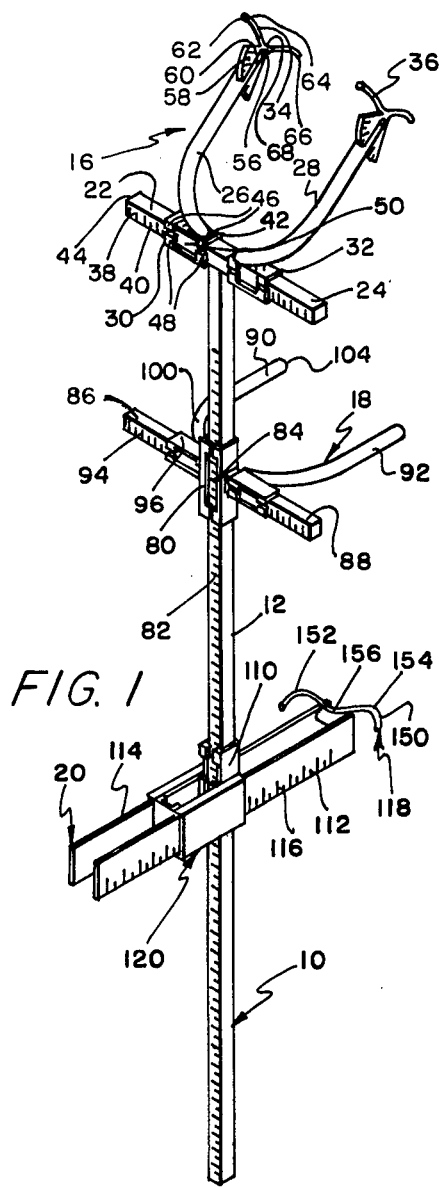
FIG. 1 is an isometric view of the instrument.
Figure 2:
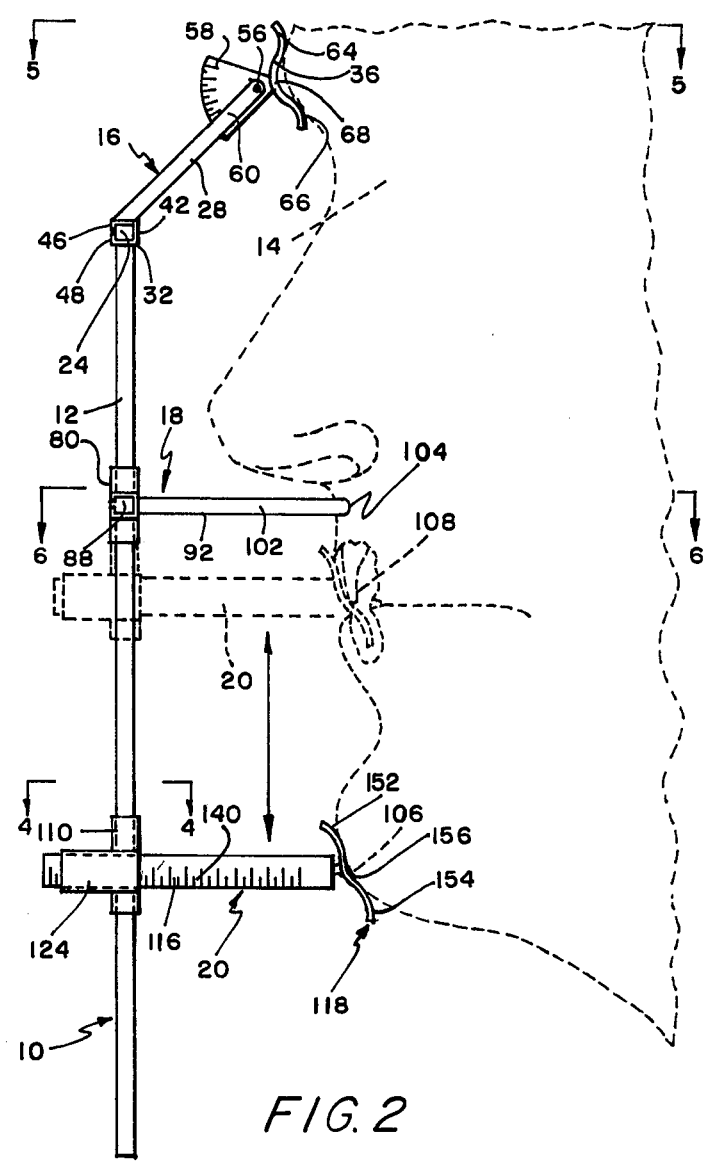
FIG. 2 is a side elevational view of the instrument as the same is applied to a patient's head that is presented in dashed outline, with an alternative position of the lowermost measuring means being shown for measuring incisor rather than chin location.
Figure 3:
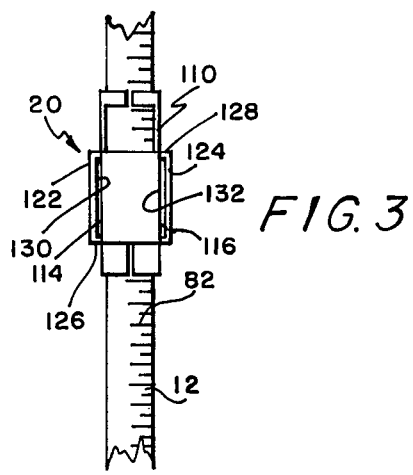
FIG. 3 is an enlarged and fragmentary detail view in front elevation of the mounting of the lowermost measuring means on the standard.
Figure 4:
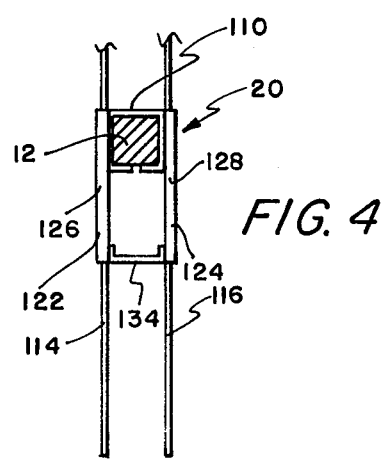
Figure 5:
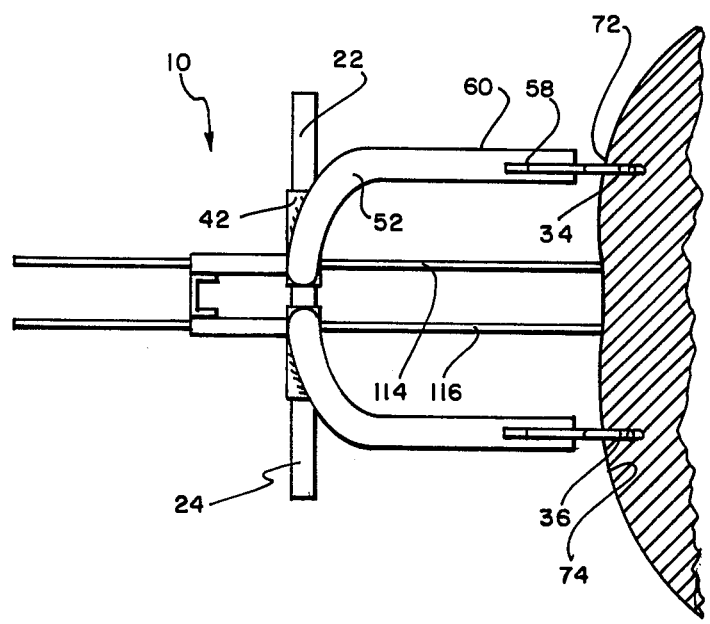
Figure 6:
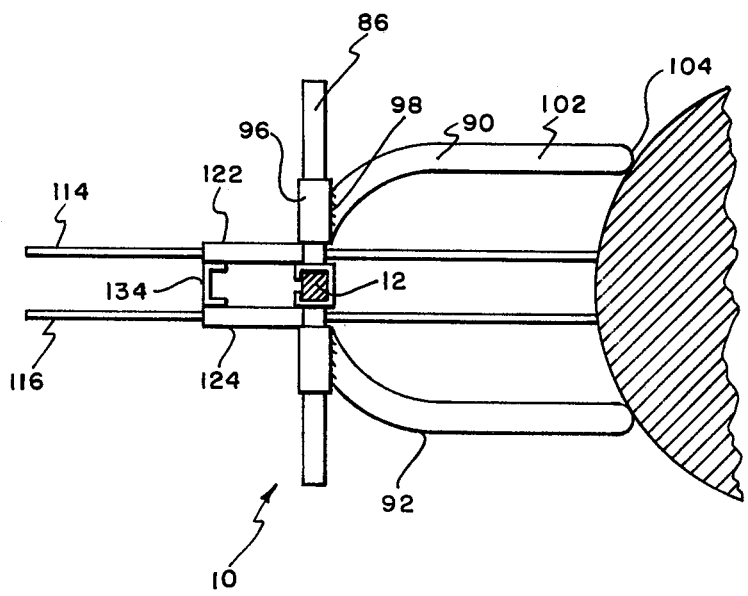

FIG. 4 is an enlarged fragmentary horizontal sectional detail view taken on the plane of the section line 4—4 in FIG. 2; and, FIGS. 5 and 6 are respectively horizontal sectional views taken on the planes of the section lines 5—5 and 6—6, with the patient's head only being partially shown.

Referring now to the drawings wherein like numbers designate like parts throughout the various views, the numeral 10 designates the occlusal instrument generally. The instrument 10 is of course made of a material suitable for surgical use in operating rooms and of a material readily lending itself to speedy and thorough sterilization such as by steam under atmospheric or superatmospheric pressure. While other metals, especially those plated with cromium, nickle and the like, and even plastic or ceramic materials might be employed largely in the instrument 10, it is thought that stainless steel is perhaps the best suited material.

The instrument 10 comprises an elongated standard 12 that will be referred to as being vertical, and which will be at least approximately vertical when used in connection with a patient whose head 14 is substantially upright. The instrument 10 also includes an orienting means carried by the standard 12 comprising an uppermost or brow measuring means 16, an intermediate or upper jaw measuring means 18, and a lowermost measuring means 20 for selectively measuring incisor and chin location.

The means 16, 18 and 20 are relatively movable vertically, whereby the spacing therebetween can be selectively varied. Consistent with such relative movement, one of such means 16, 18 and 20 can be fixed in vertical position on the standard 12, and the means 16 is so mounted on the standard 12. The means 16 comprises the upper end of the standard terminating in a "T" configuration defined by the upper end of the standard 12 having a pair of straight, aligned and oppositely extending support members 22 and 24 integral therewith.

Inasmuch as the instrument 10 has a vertical plane of symmetry that coincides with the medial plane of the head 14 of a patient during use of the instrument 10, it will be understood that the support members 22 and 24 are of equal length. The support members 22 and 24 are horizontal and normal to the plane of symmetry of the instrument 10.

The brow measuring means 16 extends rearwardly from the standard 12 and includes a pair of arms 26 and 28 movable carried respectively by the support members 22 and 24. As the support members 22 and 24 are mirror images of each other, and as the same is also true of the arm mounting means 30 and 32 of the arms 26 and 28 and of the face or brow contacting means 34 and 36 of the arms 26 and 28, a detailed description of the support member 22, arm 26, mounting means 30 and face or brow contacting means 34 will suffice for their symmetrical counterparts 24, 28, 32 and 36, respectively.

The support member 22 is of noncircular cylindrical or rectangular cross section and carries on its forward and vertical side 38 indicia 40 scribed therein in the form of a scale against which can be read the relative position of mounting means 30 on the member 22 for recordation and to enable subsequent replication of the relative position of the mounting means 30 on the member 22 at the time of initially reading the indicia 40.

The mounting means 30 comprises a channel-shaped element 42 having a sliding fit on the member 22 with its open side facing forwardly as shown. The sliding fit of the element 42 on the support member 22 is of marked frictional character, the same being snug and enhanced by the resilient character of the element 42 and its being resiliently biased so as to frictionally grip the support member 22 and to constitute means for releasably retaining the same in adjusted position. While the mounting means 30 can be slipped off the free end 44 of the support member 22 to facilitate disassembly for shipping, sterilization, etc., the element 42 is precluded from inadvertent dislodgement in normal use by the element having inturned upper and lower pairs of integral tabs 46 and 48 that overlie and which may be resiliently biased against the forward side 38 of the member 22. The tabs of the pairs 46 and 48 are spaced in the direction of the extent of the support member 22 so as to constitute a window 50 that more or less frames a part of the indicia 40 for reading the latter.

The arm 16 has one end fixedly secured by suitable brazing or the like to the top of the element 42, and the arm 26 extends rearwardly and upwardly therefrom in a direction having an initially marked lateral component and thence being curved at 52 to reduce essentially to nil the lateral divergence of the rearmost and substantially straight portion 54 of the arm 26 from the plane of symmetry of the instrument 10. The rearmost and straight portion 54 of the arm 26 is upwardly and rearwardly inclined as shown in an arrangement that is parallel to the corresponding part of the arm 28.

The rear end portion of the arm 26 is bifurcated in the vertical plane to accommodate therein for oscillatory movement the face or brow contacting means 34.

The means 34 is pivotally secured by a horizontal pivot pin 56, such means 34 including an indicia bearing segment 58 within the bifurcated portion 60 of the arm 26. The indicia of the segment 58 can be read against the arm portion 60 as to the relative angular position of the means 34 and the arm 26. The bifurcated portion 60 can resiliently be biased against the means gripped and pivotally mounted therein so that the means 34 tends to be frictionally retained against pivotal movement.

The pivots 56 of the means 34 and 36 are horizontal and in alignment. The means 34 includes an integral part in the form of a centrally joined, and curvilinear elongated brow engaging element 62. The element 62 lies in a vertical plane normal to the axis of the pivot 56 and includes rearwardly facing convex portions 64 and 66 joined by a concave portion 68.

It will suffice at this point to note that the means 34 and 36 can be adjustably spaced (preferably equally) from the medial plane of the instrument 10 so that the elements 62 can contact the brow portions 72 and 74 of the patient's head; such brow portions being forwardly convex and mating, so to speak, with the concave sections 68 of the means 34 and 36. The lateral spacing and angles of the means 34 and 36 can be read in the use of the described indicia, and the relative positions of the means 34 and 36 can be subsequently replicated quite accurately, and furthermore, such replication enables at least fairly accurate replication of the relative positions of the instrument 10, in particular the standard 12, and the patient's head.

It will be understood that the reference numerals applied to symmetrical details of the means 16 have applicability to both of the symmetrical details.

The means 18 comprises a slide 80 partially embracing the standard 12. The slide 42 is larger, but generally similar to the previously described mounting element 42 so as to engage resiliently and frictionally the standard 12, and so as to expose indicia 82 on the forward side of the standard 12 through an effective window 84 corresponding to the opening 50 of the previously described mounting element 42.

The standard 12 is of rectangular cross section and the slide 80 has a corresponding generally rectangular configuration with a pair of oppositely extending support members 86 and 88 being fixedly secured to the opposite sides of the slide 80 as shown. The support members 86 and 88 are aligned, horizontal and symmetrical. As in the case of the previously described support members 22 and 24, the members 86 and 88 are disposed to intersect the axis of the standard 12 and are of rectangular cross section.

The means 18 includes two face contacting structures 90 and 92 respectively carried by the support members 86 and 88 for adjustable movement toward and away from the medial plane of the instrument 10. As the means 18 is of symmetrical character, the same will be described in the same fashion as the means 16 so as to minimize repetition.

The support member 86 is quite similar to the member 22 and is provided indicia 94 to enable replication of the spacing or relative position of the contact element 90 with respect to the medial plane of the instrument 10.

The contact element 90 is movably supported on the support member 86 by means of a mounting member 96 to which it is fixedly secured, and the latter is similar to the mounting means 42 in that it resiliently grips and is slidable on the support member 86 against friction tending to oppose such movement.

The face contacting element 90 is of arcuate configuration so as to extend initially rearwardly and laterally outwardly from its juncture 98 with the slide or mounting element 96 as indicated at 100, and thence to extend horizontally and straight rearwardly 102 to terminate in a free end 104.

In the use of the instrument 10, as thus far described the means 16 is positioned as previously described, and the means 18 is placed so that the free ends 104 engage the face at positions immediately overlying the prominences of the maxillary arch of the upper jaw bone, it being noted that such will not normally conflict with the positioning of present or future dentures. Alternatively, the ends 104 can be positioned on and referenced to the zygomatic arches (cheekbones).

Passing now to the means 20 usable to specify both the position of the chin 106 and of the bottom of the upper incisors 108, the means 20 includes a slide 110 generally similar to the slide 80 and resiliently engaged about and frictionally gripping the standard 12. The position of the slide 110 can be read against the indicia 82 of the standard 12.

The means 20 includes a portion or extension member 112 carried by the slide 110 that is movable forwardly and rearwardly horizontally and essentially in the plane of symmetry of the instrument 10. The extension member 112 is comprised of a pair of spaced elongated and flat rails 114 and 116 disposed on opposite sides of the slide 110.

The rearmost ends of the member 112 or the rails 114 and 116 are joined by a face contacting means 118. The slide 110 is provided with means 120 for slidably guiding and supporting the rails 114 and 116 while affording a frictional drag to movement thereof. The means 120 comprises a pair of channel members 122 and 124 in opposed relation disposed on opposite sides of the slide 110 and with the free edges of their flanges 126 and 128 secured to lower portions of the opposite sides of the slide 110 so as to define guide openings 130 and 132 respectively receiving the rails 114 and 116 therethrough. In the preferred construction, the channels 122 and 124 extend forwardly of the slide and are joined at their forward ends by a vertical channel member 134. The openings 130 and 132 are dimensioned so as to accommodate a sliding but frictional fit for the rails 114 and 116. Preferably, the channels 122 and 124 have their facing sides slightly convex in the vertical plane when in repose so as to be resiliently biased against the rails 114 and 116.

The rail 116 is provided with indicia 140, which can be read against the channel 124 for replication of the extension of the rails 114 and 116 whenever desired.

The contacting means 118 includes an elongated curvilinear element 150 disposed in the medial plane of the instrument 10 that is generally inclined rearwardly and downwardly and which includes convex extreme upper and lower portions 152 and 154 that are smoothly joined and merge with an intermediate concave portion 156.

The contacting element 150 is such that the chin can be seated in the concave seat or portion 156 when the means 20 is in the full line position shown in FIG. 2 and against the lower edge of the upper front incisors 108 when the means 20 is in its alternative position shown in dashed outline in FIG. 2.

The use of the instrument 10 will be readily and abundantly clear to those of modest familiarity with the art.

Having once established the positioning of all adjustable or movable parts of the instrument 10 when fitted against the patient's face (means 20 having been placed in each of its measuring modes relative to chin and upper teeth) and all pertinent readings of all indicia recorded, the patient's lower jaw being disposed in its desired or natural position of mouth closure, the instrument 10 can at any time thereafter have the position of its relative movable parts replicated. With such replication, the patient's face, particularly the lower jaw, can be manipulated to return the same to the same condition as when originally measured. Not only can the lower jaw be repositioned to its desired exact location, but the exact relative position of the upper incisors can be established.

Thus, the instrument 10, which can be easily disassembled for thorough cleaning and sterilization, enables great precision in restorative facial work and in the preparation of dentures, total or partial.

Reference should be made to the appended claims to ascertain the actual scope of the invention.

I claim:

1. In an occlusal instrument, an upstanding elongated standard adapted to be positioned in spaced relation at the front of and in the medial plane of a patient's head, said standard carrying orienting means adapted to engage spaced regions of the patient's face, said orienting means comprising uppermost, intermediate and lowermost measuring means mounted on the standard for movement relative to each other in the direction of the longitudinal extent of the standard, a first indicia means for enabling reading of the relative positions of the uppermost, intermediate and lowermost measuring means along the extent of the standard whereby such relative positions can be replicated, each of said measuring means extending rearwardly from the standard and terminating in patient contacting means, at least one of said measuring means being provided with means for varying the rearward extent and the spacing of its contacting means from the standard, a second indicia means for enabling replication of the extent of said one measuring means, and at least one of the other measuring means including a pair of horizontally spaced and rearwardly extending arms with the face contacting means of such measuring means including symmetrical parts disposed at the rearmost extremities of the arms, means carried by and movable with said one of the other measuring means for enabling horizontal and lateral movement of the arms relative to the standard, whereby the horizontal and lateral spacing of the said symmetrical parts can be varied, a third indicia means for enabling replication of the horizontal and lateral positions of the arms relative to the standard, said one measuring means comprising a slide for vertical movement on the standard, with said slide including a resilient element resiliently bearing against the standard in an arrangement such that friction therebetween opposes such vertical movement thereby releasably retaining the slide in a selected vertical position, said one measuring means including a pair of elongated and rearwardly extending parallel rails that are joined at their rearmost extremities by the patient contacting means of such means, said rails being disposed on opposite sides of the standard, with said slide having a pair of openings therethrough on opposite sides of the standard that slidably and guidingly receive the rails therethrough.

2. The combination of claim 1, wherein the patient contacting means of said one of the measuring means has a contacting surface that is concave and which faces rearwardly and upwardly relative to the extent of the standard and which surface is adapted for selective engagement with the upper incisors and the chin of a patient.

3. In an occlusal instrument, an upstanding elongated standard adapted to be positioned in spaced relation at the front of and in the medial plane of a patient's head, said standard carrying orienting means adapted to engage spaced regions of the patient's face, said orienting means comprising uppermost, intermediate and lowermost measuring means mounted on the standard for movement relative to each other in the direction of the longitudinal extent of the standard, a first indicia means for enabling reading of the relative positions of the uppermost, intermediate and lowermost measuring means along the extent of the standard whereby such relative positions can be replicated, each of said measuring means extending rearwardly from the standard and terminating in patient contacting means, at least one of said measuring means being provided with means for varying the rearward extent and the spacing of its contacting means from the standard, a second indicia means for enabling replication of the extent of said one measuring means, and at least one of the other measuring means including a pair of horizontally spaced and rearwardly extending arms with the face contacting means of such measuring means including symmetrical parts disposed at the rearmost extremities of the arms, means carried by and movable with said one of the other measuring means for enabling horizontal and lateral movement of the arms relative to the standard, whereby the horizontal and lateral spacing of the said symmetrical parts can be varied, a third indicia means for enabling replication of the horizontal and lateral positions of the arms relative to the standard, each of said symmetrical parts being pivotally mounted on its respective arm, whereby the same are adapted to be swung to pivotal positions best conforming with the contours of contacted portions of the face, and a third indicia means enabling replication of the pivotal positions of the symmetrical parts.

4. The combination of claim 3, wherein the symmetrical parts are pivotally mounted for movement about aligned horizontal axes.

5. The combination of claim 3, wherein said one of the other measuring means is the uppermost measuring means, and wherein said one measuring means is the lowermost measuring means.

6. The combination of claim 5, wherein the uppermost measuring means is immovably mounted on the standard relative to the elongated extent of the standard.

7. In an occlusal instrument, an upstanding elongated standard adapted to be positioned in spaced relation at the front of and in the medial plane of a patient's head, said standard carrying orienting means adapted to engage spaced regions of the patient's face, said orienting means comprising uppermost, intermediate and lowermost measuring means mounted on the standard for movement relative to each other in the direction of the longitudinal extent of the standard, a first indicia means for enabling reading of the relative positions of the uppermost, intermediate and lowermost measuring means along the extent of the standard whereby such relative positions can be replicated, each of said measuring means extending rearwardly from the standard and terminating in patient contacting means, at least one of said measuring means being provided with means for varying the rearward extent and the spacing of its contacting means from the standard, a second indicia means for enabling replication of the extent of said one measuring means, and at least one of the other measuring means including a pair of horizontally spaced and rearwardly extending arms with the face contacting means of such measuring means including symmetrical parts disposed at the rearmost extremities of the arms, means carried by and movable with said one of the other measuring means for enabling horizontal and lateral movement of the arms relative to the standard, whereby the horizontal and lateral spacing of the said symmetrical parts can be varied, a third indicia means for enabling replication of the horizontal and lateral positions of the arms relative to the standard, said one of the other measuring means comprising a slide mounted for vertical movement on the standard, with said slide including a resilient element bearing against the standard in an arrangement such that friction therebetween opposes such vertical movement thereby for releasably retaining the slide in a selected vertical position, said means for enabling horizontal and lateral movement of the arms comprising said slide having aligned oppositely extending support members fixed thereto at positions on opposite sides of the standard, and said arms each having a guide means embracing and resiliently gripping one of the support members slidably received therethrough.

8. The combination of claim 7, wherein each of the symmetrical parts is pivotally mounted on its respective arm, whereby the same are adapted to be swung to pivotal positions best conforming with the contours of contacted portions of a patient and a third indicia means enabling replication of the pivotal positions of the symmetrical parts.

* * * * *